United States Patent
Hollender et al.

(10) Patent No.: US 11,406,360 B2
(45) Date of Patent: Aug. 9, 2022

(54) ULTRASOUND TRANSDUCERS FOR CONSTRUCTIVE SHEAR WAVE INTERFERENCE AND RELATED METHODS AND SYSTEMS

(71) Applicant: Duke University, Durham, NC (US)

(72) Inventors: Peter J. Hollender, Durham, NC (US); Mark Palmeri, Durham, NC (US)

(73) Assignee: Duke University, Durham, NC (US)

( * ) Notice: Subject to any disclaimer, the term of this patent is extended or adjusted under 35 U.S.C. 154(b) by 411 days.

(21) Appl. No.: 16/310,967

(22) PCT Filed: Jun. 22, 2017

(86) PCT No.: PCT/US2017/038742
§ 371 (c)(1),
(2) Date: Dec. 18, 2018

(87) PCT Pub. No.: WO2017/223312
PCT Pub. Date: Dec. 28, 2017

(65) Prior Publication Data
US 2020/0305841 A1 Oct. 1, 2020

Related U.S. Application Data

(60) Provisional application No. 62/353,161, filed on Jun. 22, 2016.

(51) Int. Cl.
*A61B 8/08* (2006.01)
*A61B 8/00* (2006.01)
(Continued)

(52) U.S. Cl.
CPC ............ *A61B 8/485* (2013.01); *A61B 8/4494* (2013.01); *G01S 7/52022* (2013.01);
(Continued)

(58) Field of Classification Search
CPC ....... A61B 8/4477; A61B 8/4494; A61B 8/54; G01S 15/8922; G01S 15/8927; G01S 7/52022; G01S 7/52079
See application file for complete search history.

(56) References Cited

U.S. PATENT DOCUMENTS

| 6,764,448 B2 | 7/2004 | Trahey et al. |
| 8,118,744 B2 | 2/2012 | Palmeri et al. |
(Continued)

FOREIGN PATENT DOCUMENTS

| WO | 2012/116364 | 8/2012 |
| WO | 20160196631 | 12/2016 |

OTHER PUBLICATIONS

Extended European Search Report for corresponding EP Application No. 17816207.9 dated Jan. 17, 2020, 9 pages.
(Continued)

*Primary Examiner* — Amelie R Davis
(74) *Attorney, Agent, or Firm* — Myers Bigel, P.A.

(57) ABSTRACT

A transducer array includes at least one annular shear wave generation transducer that defines an interior area, the at least one annular shear wave generation transducer being configured to generate a shear wave excitation to a region of interest such that the shear wave excitation excites at least a part of a corresponding cylindrical portion of the region of interest and shear waves propagating from the cylindrical portion of the region of interest constructively interfere in an interior region of the cylindrical portion of the region of interest: and at least one tracking transducer positioned in the interior area of the at least one annular shear wave generation transducer, the at least one tracking transducer being configured to detect a shear wave in the interior region of the region of interest.

21 Claims, 12 Drawing Sheets

(51) Int. Cl.
*G01S 15/89* (2006.01)
*G01S 7/52* (2006.01)
(52) U.S. Cl.
CPC ...... *G01S 7/52079* (2013.01); *G01S 15/8922* (2013.01); *G01S 15/8927* (2013.01)

(56) References Cited

U.S. PATENT DOCUMENTS

| | | |
|---|---|---|
| 2010/0331869 A1* | 12/2010 | Voegele .............. A61B 8/4494 606/169 |
| 2011/0184287 A1 | 7/2011 | McAleavey |
| 2011/0201931 A1 | 8/2011 | Palmeri et al. |
| 2012/0136250 A1 | 5/2012 | Tabaru et al. |
| 2012/0293044 A1 | 11/2012 | Bromfield |
| 2013/0051178 A1 | 2/2013 | Rybyanets |
| 2013/0211253 A1 | 8/2013 | Hsu et al. |
| 2013/0218012 A1 | 8/2013 | Specht et al. |
| 2014/0046173 A1* | 2/2014 | Greenleaf .............. G16H 50/30 600/411 |
| 2015/0165243 A1 | 6/2015 | Slayton et al. |
| 2015/0305717 A1 | 10/2015 | Hollender et al. |

OTHER PUBLICATIONS

International Search Report and Written Opinion for PCT/US2017/038742 dated Sep. 6, 2017, 9 pages.

\* cited by examiner

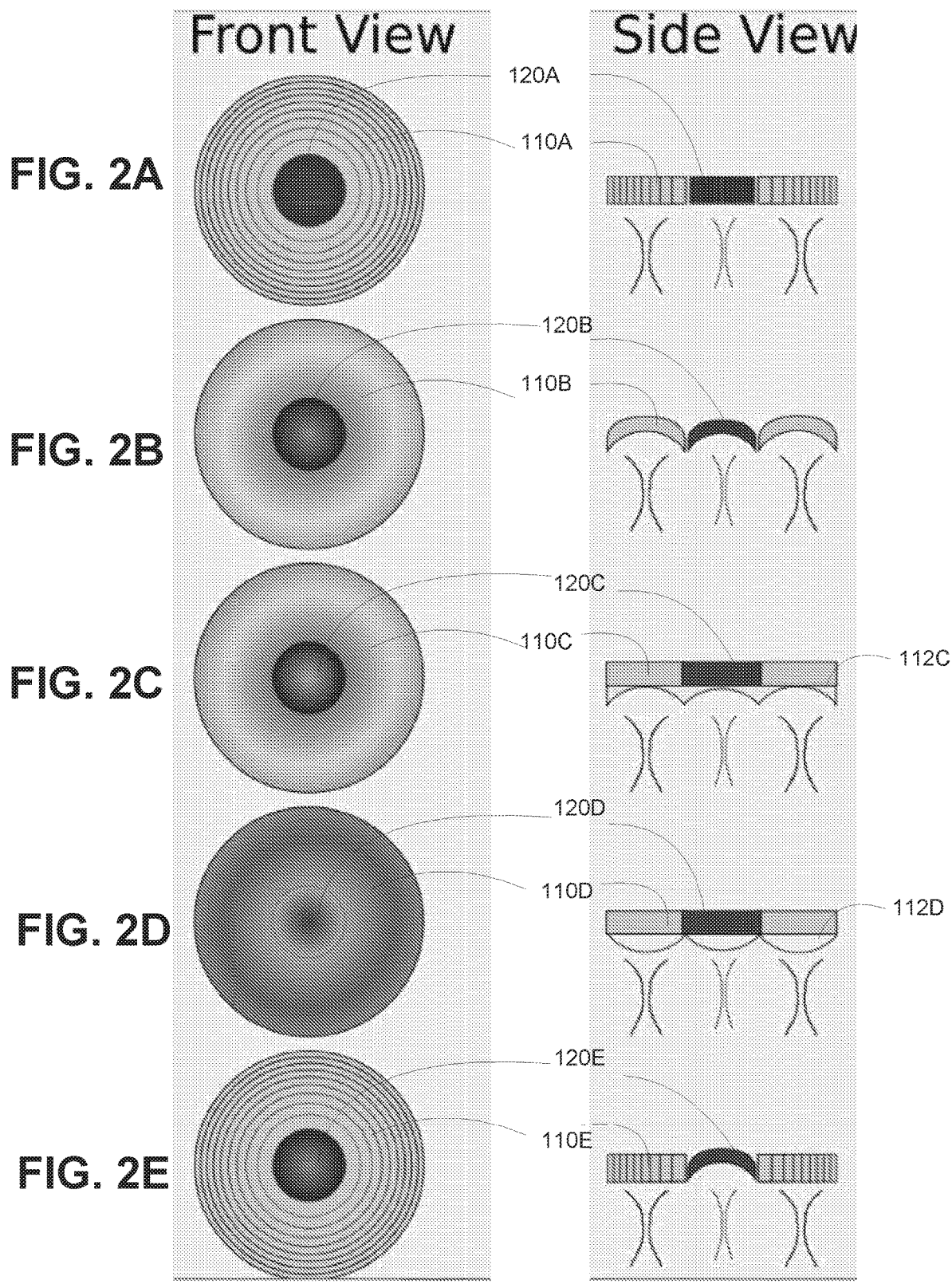

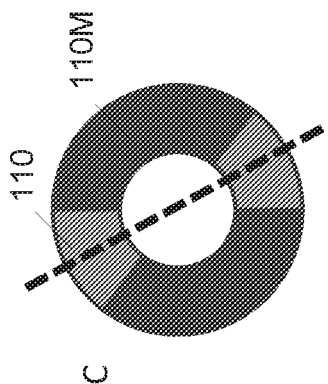
FIG. 3A
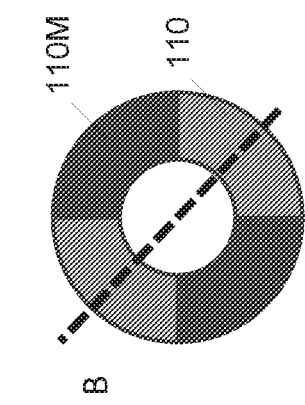
FIG. 4A
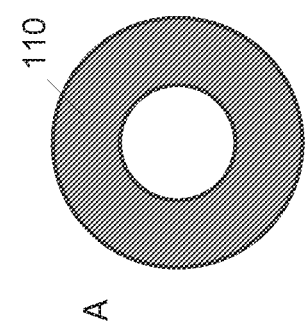
FIG. 5A
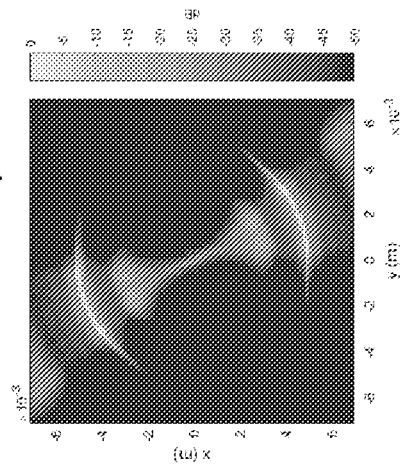
FIG. 3B
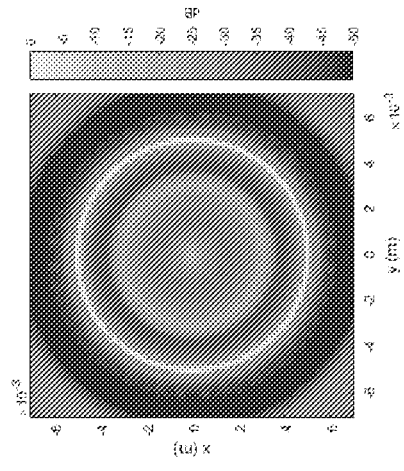
FIG. 4B
FIG. 5B

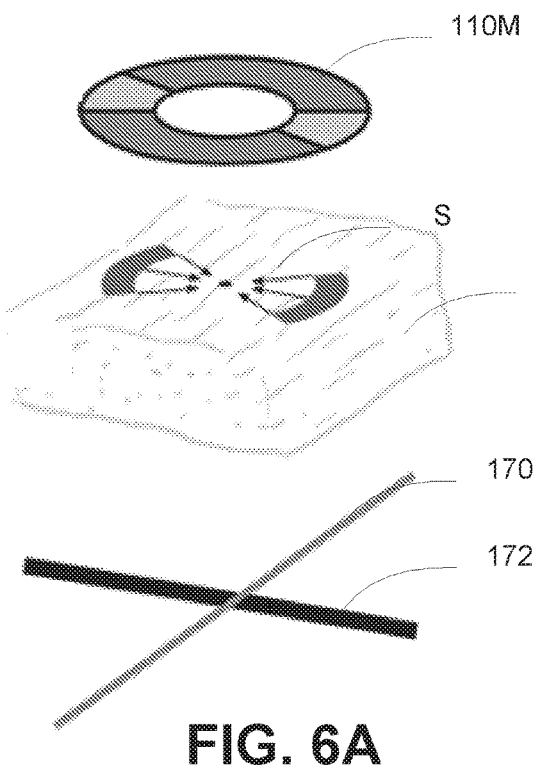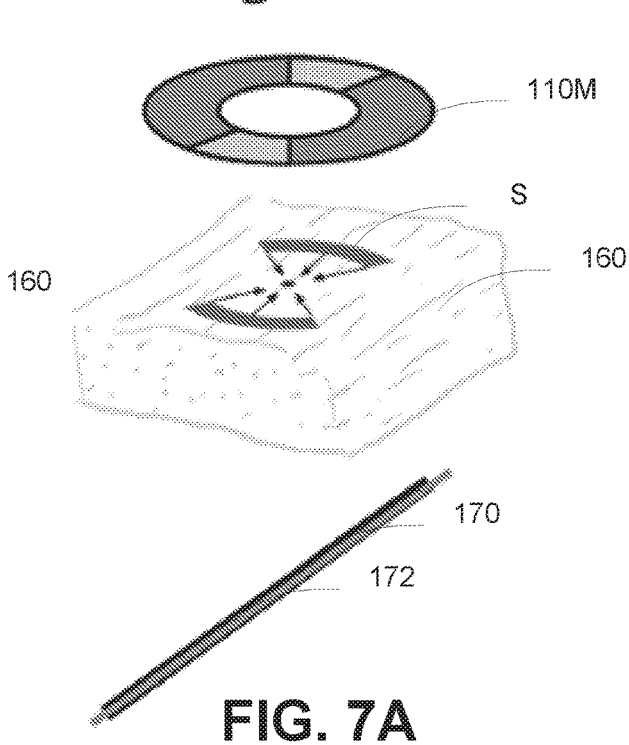
FIG. 6A
FIG. 7A
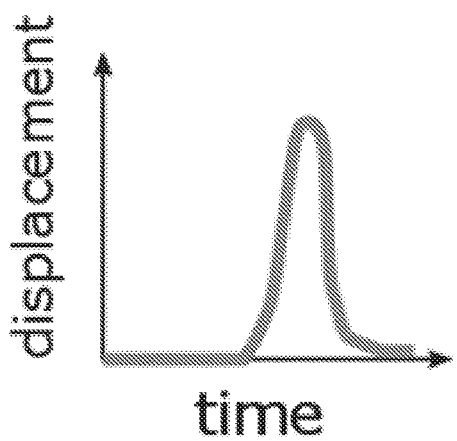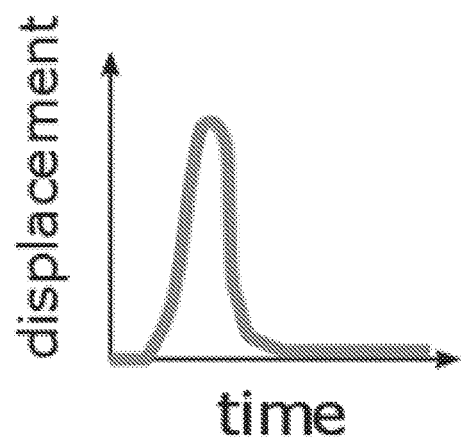
FIG. 6B
FIG. 7B

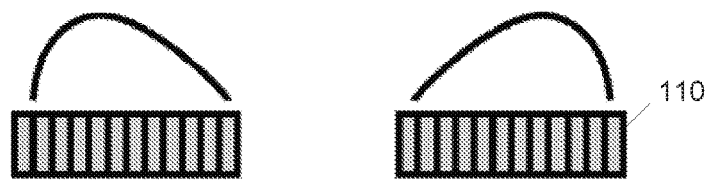
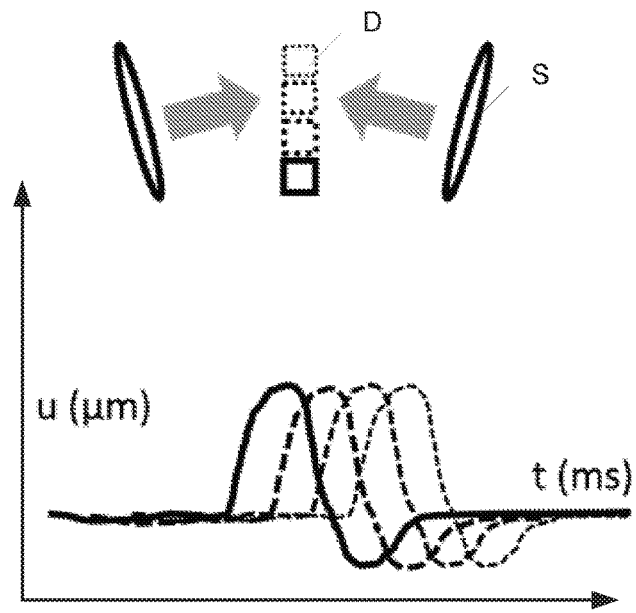
FIG. 10A
FIG. 10B
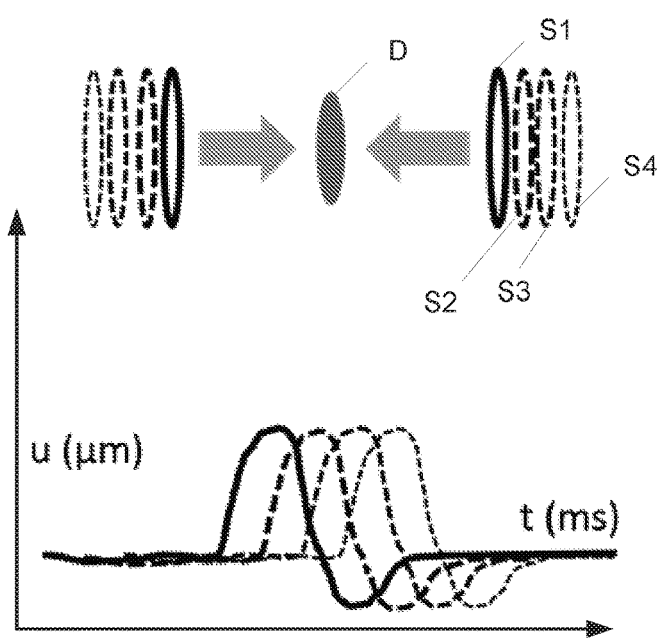
FIG. 11A
FIG. 11B

FIG. 15
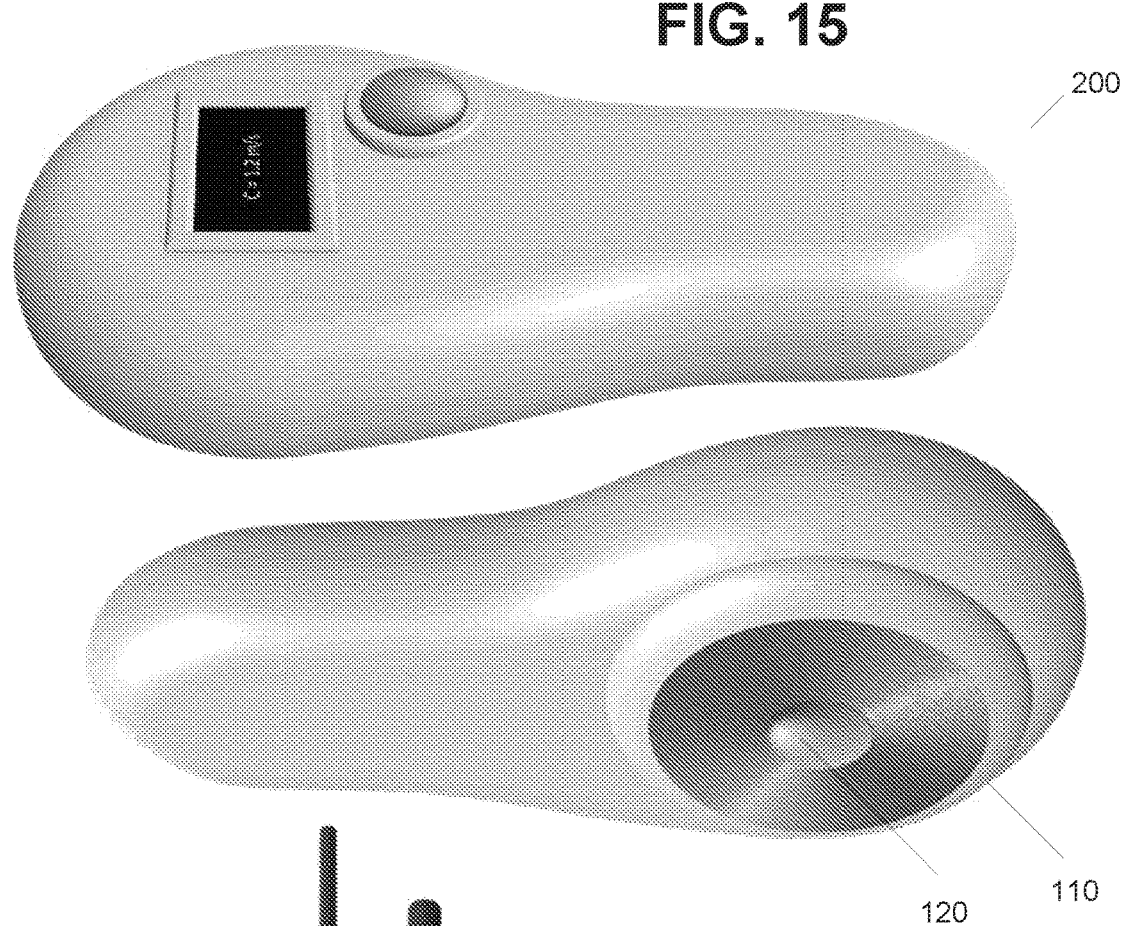
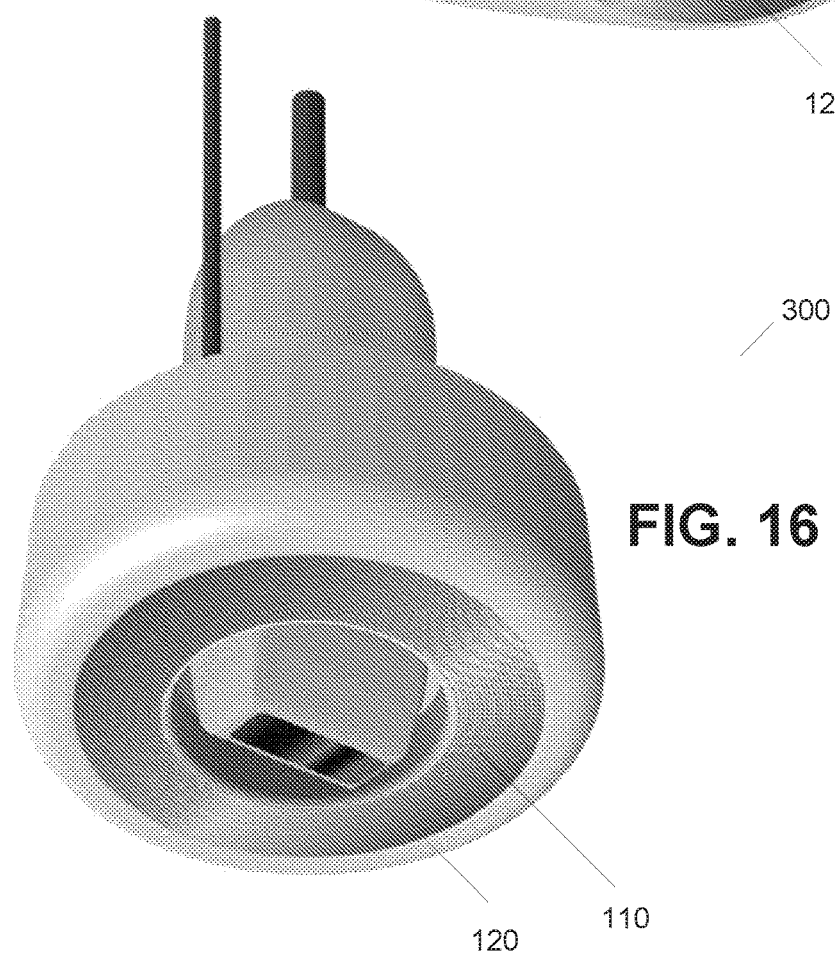
FIG. 16

ULTRASOUND TRANSDUCERS FOR CONSTRUCTIVE SHEAR WAVE INTERFERENCE AND RELATED METHODS AND SYSTEMS

RELATED APPLICATIONS

This application is a 35 U.S.C. § 371 national stage application of PCT International Application No. PCT/US2017/038742, filed Jun. 22, 2017, which application claims priority to U.S. Provisional Application 62/353,161, filed Jun. 22, 2016, the disclosures of which are hereby incorporated by reference in their entireties.

FIELD OF THE INVENTION

The present invention relates to ultrasound transducers, and in particular, to ultrasound transducers and related systems for generating constructive shear wave interference.

BACKGROUND

Acoustic Radiation Force (ARF) shear wave elasticity imaging methods typically use a transverse propagation velocity of mechanical shear waves in materials to estimate mechanical properties of a sample, such as material elasticity constants. These techniques may be adapted into imaging systems to compute the local shear wave propagation velocity as a function of both axial and lateral position. The velocity may be calculated by estimating the differences in arrival times of the shear waves, either at different recording locations or from different excitation locations.

For example, acoustic, radiation force (ARF) arises from a transfer of momentum from a sound wave to the medium through which it is traveling due to, both absorption and scattering of the wave and is described by K. R. Nightingale, M. Palmeri, R. Nightingale, and Trahey, "On the feasibility of remote palpation using acoustic radiation force," J Acoust Soc Am, vol. 110, pp. 625-634, 2001 and G. R. Torr, "The Acoustic Radiation Force," Am. J. Phys., vol. 52, pp. 402-408, 1984.

$$\vec{F} = \frac{2\alpha \vec{I}}{c} \quad (1)$$

where α is the acoustic attenuation, I is the acoustic intensity, c is the speed of sound, and F is the force applied to the medium. Ultrasonic Shear Wave Elasticity Imaging (SWEI) utilizes this acoustic radiation force by applying ultrasonic pushing pulses that displace the tissue on the order of microns and tracking the propagation of the transverse wave that propagates away from the region of excitation.

SWEI is currently used to characterize the stiffness of tissues, including liver fibrosis. Initial implementations of SWEI involved using sparse displacement fields in inverted wave equation solutions, or time-of-flight algorithms, in which shear wave arrival times are estimated at multiple spatial locations with an assumed direction of propagation. See Palmeri, M. H. Wang, J. J. Dahl, K. D. Frinkley, K. R. Nightingale, and L. Zhai "Quantifying Hepatic Shear Modulus in Vivo Using Acoustic Radiation Force. Accept. UMB, 34(4):546-558 (April 2008). Additional improvements to SWEI include using multiple shear wave sources that can create a unique shear wave morphology that can be tracked at a single location using correlation-based methods, with the benefit of reduced shear wave speed estimation variance. See U.S. Pat. No. 8,225,666 and U.S. Patent Publication No. 2011/0184,287, the disclosures of which are hereby incorporated by reference in their entireties.

Currently used SWEI techniques that utilize acoustic radiation force to generate shear waves typically require diagnostic ultrasound arrays to generate and track shear waves, with significant signal processing overhead to calculate shear wave arrival times and to estimate shear wave speeds.

U.S. Pat. Nos. 8,753,277 and 8,225,666 to McAleavey discuss a spatially-modulated source function to estimate shear velocity from a single recording location, and extended the method to create images in using a fixed spatial distance between the source functions and the receive location.

A shear wave created through conventionally focused ultrasound originates from a focal spot about the size of a grain of rice and propagates transversely away from the focal spot. As a result of this geometric spreading, the amplitude of the wave measured in the field of interest is inversely proportional to the square root of the distance from its origin, limiting the usable propagation distances and/or necessitating higher intensity excitations to generate larger waves.

SUMMARY OF EMBODIMENTS OF THE INVENTION

In some embodiments, a transducer array includes at least one annular shear wave generation transducer that defines an interior area, the at least one annular shear wave generation transducer being configured to generate a shear wave excitation to a region of interest such that the shear wave excitation excites at least a part of a corresponding cylindrical portion of the region of interest and shear waves propagating from the cylindrical portion of the region of interest constructively interfere in an interior region of the cylindrical portion of the region of interest; and at least one tracking transducer positioned in the interior area of the at least one annular shear wave generation transducer, the at least one tracking transducer being configured to detect a shear wave in the interior region of the region of interest.

In some embodiments, the at least one annular shear wave generation transducer has a higher extensional strain constant than the at least one tracking transducer.

In some embodiments, the at least one annular shear wave generation transducer comprises an array of concentric annular transducers configured to transmit excitation pulses to excite at least a part of the cylindrical portion of the region of interest, wherein the shear wave excitation comprises the excitation pulses.

In some embodiments, the at least one annular shear wave generation transducer comprises a concave annular transducer configured to focus the shear wave excitation to excite the cylindrical portion of the region of interest.

In some embodiments, the transducer array includes a focusing lens on a face of the annular shear wave generation transducer configured to focus the shear wave excitation to excite at least a part of the cylindrical portion of the region of interest.

In some embodiments, the at least one tracking transducer comprises an array of concentric tracking transducers.

In some embodiments, the at least one tracking transducer comprises a concave tracking element.

In some embodiments, the transducer array comprises a focusing lens on a face of the at least one tracking transducer configured to focus a tracking pulse to the interior region of the region of interest where shear waves generated by the shear wave excitation constructively interfere.

In some embodiments, the transducer array comprises an apodized portion of the annular shear wave generation transducer, wherein the apodized portion has a reduced or eliminated a shear wave excitation therefrom such that the annular shear wave generation transducer excites a part of the cylindrical portion of the region of interest.

In some embodiments, a transducer array assembly includes a transducer array comprising: at least one annular shear wave generation transducer that defines an interior area; and at least one tracking transducer positioned in, the interior area of the at least one annular shear wave generation transducer; and a controller configured to control the at least one annular shear wave generation transducer to generate a shear wave excitation to a region of interest such that the shear wave excitation excites at least a part of a corresponding cylindrical portion of the region of interest and shear waves propagating from the cylindrical portion of the region of interest constructively interfere in an interior region of the cylindrical portion of the region of interest and to control the at least one tracking transducer to detect a shear wave in the interior region of the region of interest.

In some embodiments, the at least one annular shear wave generation transducer has a higher extensional strain constant than the at least one tracking transducer.

In some embodiments, the at least one annular shear wave generation transducer comprises an array of concentric annular transducers configured to transmit excitation pulses to excite at least a part of the cylindrical portion of the region of interest, wherein the shear wave excitation comprises the excitation pulses.

In some embodiments, the at least one annular shear wave generation transducer comprises a concave annular transducer configured to focus the shear wave excitation to excite at least a part of the cylindrical portion of the region of interest.

In some embodiments, the transducer array includes a focusing lens on a face of the annular shear wave generation transducer configured to focus the shear wave excitation to excite at least a part of the cylindrical portion of the region of interest.

In some embodiments, the at least one tracking transducer comprises an array of concentric tracking transducers.

In some embodiments, the at least one tracking transducer comprises a concave tracking, element.

In some embodiments, the transducer array comprises a focusing lens on a face of the at least one tracking transducer configured to focus a tracking pulse to the interior region of the region of interest where shear waves generated by the shear wave excitation constructively interfere.

In some embodiments, the controller is configured to control the at least one tracking transducer to detect a shear wave in the interior region of the region of interest by emitting at least one tracking pulse In some embodiments, the transducer array comprises an apodized portion of the annular shear wave generation transducer, wherein the apodized portion has a reduced or eliminated a shear wave excitation therefrom.

In some, embodiments, the controller is configured to control a signal to the apodized portion of the annular shear wave generation transducer to reduced or eliminate the shear wave excitation therefrom.

In some embodiments, the transducer array comprises a mask configured to reduced or eliminate the shear wave excitation from the apodized portion of the annular shear wave generation transducer.

In some embodiments, the controller is further configured to characterize the region of interest based on the constructive shear wave detected by the at least one tracking transducer.

In some embodiments, a method of generating a constructive shear wave for characterizing a region of interest includes providing a transducer array comprising: at least one annular shear wave generation transducer that defines an interior area; and at least one tracking transducer positioned in the interior area of the at least one annular shear wave generation transducer; and controlling the at least one annular shear wave generation transducer to generate a shear wave excitation to a region of interest such that the shear wave excitation excites at least a part of a corresponding cylindrical portion of the region of interest and shear waves propagating from the cylindrical portion of the region of interest constructively interfere in an interior region of the cylindrical portion of the region of interest; and controlling at least one tracking transducer to detect a shear wave in the interior region of the region of interest.

BRIEF DESCRIPTION OF THE DRAWINGS

The accompanying drawings, which are incorporated in and constitute a part of the specification, illustrate embodiments of the invention and, together with the description, serve to explain principles of the invention.

FIGS. 2A-2F are front and side views of ultrasound transducers according to some embodiments.

FIGS. 3A, 4A and 5A are front views of an annular ultrasound shear wave generation transducer according to some embodiments. FIGS. 3B, 4B and 5B illustrated corresponding shear wave propagation from the annular ultrasound shear wave generation transducers of FIGS. 3A, 4A and 5A, respectively.

FIGS. 6A and 7A are schematic diagrams of a shear wave generated by a shear wave generation transducer in a material according to some embodiments. FIGS. 6B and 7B are corresponding graphs of the time and displacement of the shear wave displacement resulting from the configurations shown in FIGS. 6A and 7A, respectively.

FIGS. 8A, 9A 10A and 11A are schematic diagrams of an annular transducer and a shear wave generated by the annular shear wave generation transducer according to some embodiments. FIGS. 8B, 9B, 10B and 11B are corresponding graphs of the time and displacement of the shear wave displacement resulting from the configurations shown in FIGS. 8A, 9A, 10A and 11A, respectively.

FIG. 15 is a perspective front and side view of an integrated hand-held transducer according to some embodiments.

FIG. 16 is a perspective front view of an annular transducer that is added to a conventional tracking transducer according to some embodiments.

DETAILED DESCRIPTION OF THE EMBODIMENTS OF THE INVENTION

Figure 1:
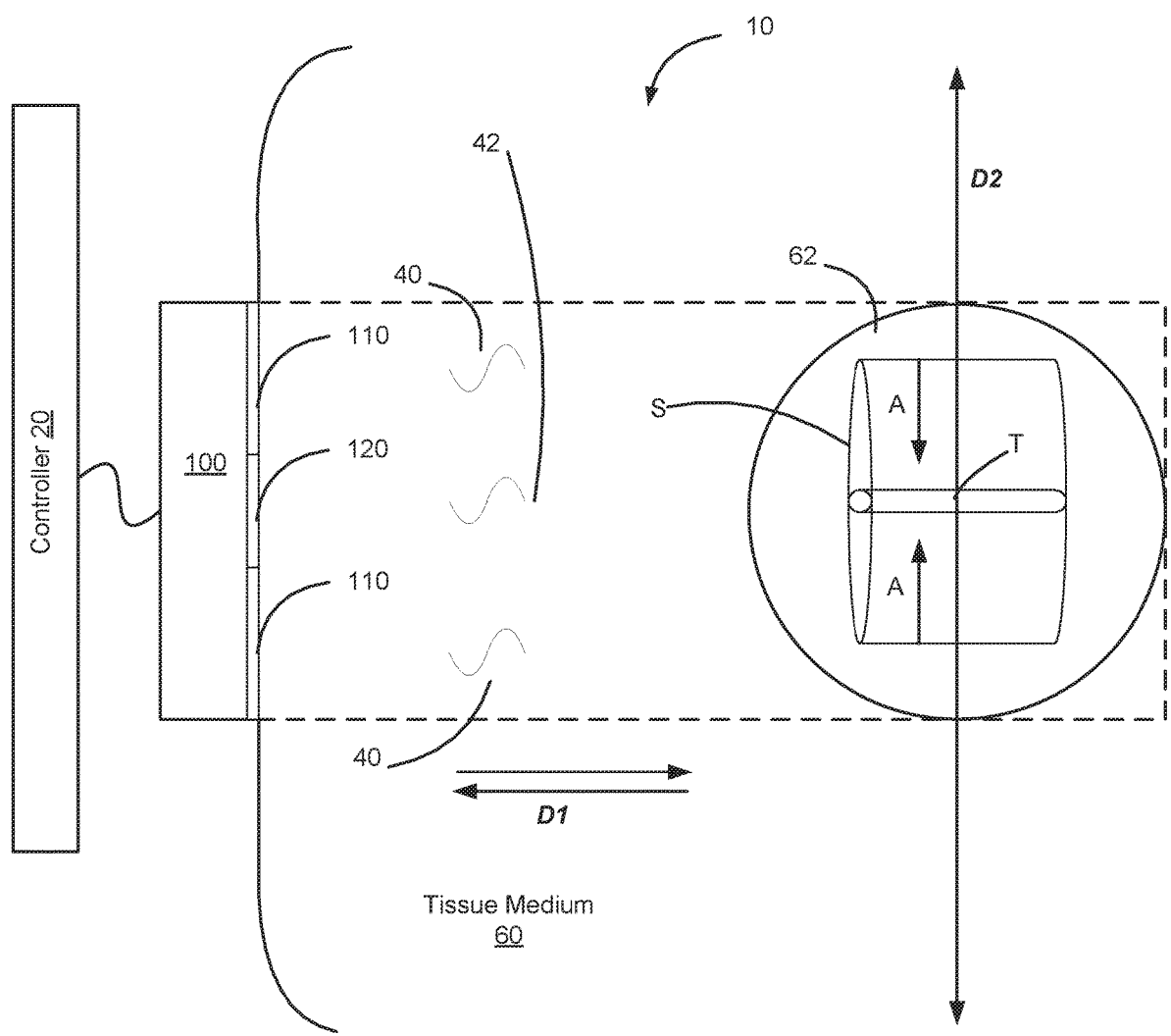
FIG. 1 is a schematic diagram of ultrasound systems, methods and computer program products according to some embodiments.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are; intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one, or more of the associated listed items. As used herein, phrases such as "between X and Y" and "between about X and Y" should be interpreted to include X and Y. As used herein, phrases such as "between about X and Y" mean "between about X and about Y," As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. For example, the term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be, for example but not limited to, an electronic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM).

Embodiments according to the present invention are described herein with reference to the term "tissue." It will be understood that the term tissue can include biological materials, such as, blood, organs, vessels and other biological objects found in a body. It will be further understood that embodiments according to the present invention may be applicable to humans as well as other species. Embodiments according to the present invention may also be utilized to image objects other than tissue.

It will be understood that the scope of the present invention includes, for example, two dimensional (2D) ultrasound imaging and 3D (or volumetric) ultrasound imaging. In addition, the components of the ultrasound imaging described herein may be packaged as a single unit or packaged separately and interconnected to provide the functions described herein.

Embodiments according to the present invention are also described by reference to Acoustic Radiation Force imaging (ARFI) which is described in greater detail, for example, in U.S. Pat. No. 6,371,912, the entire disclosure of which is incorporated herein by reference. An acoustic radiation force may be used to apply a force to tissue thereby causing the tissue to move in the direction of the force and/or to generate a shear wave.

As used herein, a "shear wave" is a form of sample displacement in which a shear wave source, such as ultrasound energy, is transmitted into the sample in one direction and generates an extended shear wave the propagates in another direction that is substantially orthogonal to the direction of the shear wave source. The displacement caused by a shear wave source may be in a range between about 0.1 µm and about 300 µm. Other displacements can be provided.

The term "time of arrival" refers herein to the measured time at which a feature of the shear wave reaches a predefined location. The time of arrival is measured by conventional measurement techniques.

As illustrated in FIG. 1, an ultrasound system 10 includes a controller 20 and an ultrasound transducer array 100. The ultrasound transducer array 100 includes an annular shear wave generation transducer 110 and a tracking transducer 120 positioned in an interior or central region of the transducer array 100. The ultrasound transducers 110, 120 may be configured to transmit and receive ultrasound signals in a direction D1, and may be contacted to a target medium such as a tissue medium 60. As illustrated, the tissue medium 60 includes a target region 62. The shear wave generation transducer 110 may include one or more elements that are configured to transmit sufficient, ultrasound energy, for example, by applying an impulse excitation acoustic radiation force to the medium 60, to generate a shear wave that propagates in a direction D2 that is orthogonal to D1. The tracking transducer 120 may be configured to transmit and receive lower energy ultrasound signals to interrogate the region of interest 62, for example, using ARFI or B-mode imaging techniques to monitor the tissue through time before and/or after the shear wave excitation force has been applied. ARFI imaging is, discussed in U.S. Pat. Nos. 6,371,912; 6,951,544 and 6,764,448, the disclosures of which are hereby incorporated by reference in their entireties. Shear waves are discussed in U.S. Pat. Nos. 8,118,744 and 6,764,448, the disclosures of which are hereby incorporated by reference in their entireties.

As illustrated in FIG. 1, the controller 20 is configured to control the annular shear wave generation transducer 110 to generate a shear wave excitation 40 to the region of interest 62 such that the shear wave excitation excites a corresponding hollow cylindrical portion S for shear wave excitation in the region of interest 62 to form shear waves that propagate from the cylindrical portion S. Shear waves propagating from the cylindrical portion S of the region of interest 62 travel in part along, arrow A and constructively interfere in an interior region T of the cylindrical portion S of the region of interest 62. The controller is also configured to control the tracking transducer 120 to transmit and receive lower energy ultrasound signals 42 to interrogate the region of interest 62 to detect a shear wave in the interior region T where the shear waves constructively interfere in the interior area of the cylindrical excitation portion S.

In some embodiments, the annular shear wave generation transducer 110 may be configured to excite the cylindrical portion S as shown in FIG. 1 by focusing the ultrasound signal in cylindrical coordinates such that the cylindrical portion S has a height of between 0.5 mm and 5 cm and a diameter between 1 mm and 5 cm and a thickness between 0.02 mm and 5 mm. Various embodiments that can be used for the transducers 110 and 120, which can be used to excite a cylindrical portion S are shown in FIGS. 2A-2E. In FIG. 2A, the shear wave generation transducer is provided by an array of transducers 110A with the tracking transducer 120A in the center region of the array of transducers 110A. Excitations in the array of transducers 120A may be initiated with a timing selected to focus the resulting excitation pulse at various depths to form the cylindrical shape shown by cylindrical portion S in FIG. 1. As illustrated in FIG. 2B, the shear wave generation transducer 110B and the tracking transducer 120B are shaped with a concave shape to focus the excitation beam along a cylindrical shape in the region of interest using a single excitation pulse without necessarily requiring a plurality of delayed excitation pulses to focus the pulse at a particular depth and diameter. As shown in FIG. 2C, a concave focusing lens 112C may be positioned on the shear wave generation transducer 110C and the tracking transducer 120C, or as shown in FIG. 2D, a convex focusing lens 112D may be positioned on the shear wave generation transducer 110D and the tracking transducer 120D. The lenses 112C, 112D may focus the excitation and/or tracking beams from the transducers 110C, 110D, 120C, 120D as shown in FIG. 1 to excite and track tissue along the height of the cylindrical portion S.

It should be understood that the various shear wave generation transducers and tracking transducers of FIGS. 2A-2D may be interchangeably combined with one another. For example, as illustrated in FIG. 2E, a concave tracking transducers 120E may be combined with an array of concentric shear wave generation transducers 110E.

Moreover, in some embodiments, the transducers of FIGS. 2A-2E may be sized and shaped to deliver a shear wave of a given dimension or range of dimensions. For example, the thickness and diameter of the array of transducers 110A in FIG. 2A and the time delay and power at which the transducers 110A are actuated may determine the size and shape of the resulting shear wave. Moreover, the size and shape of the lenses 112C, 112D together with the size and shape of the transducers 110C, 110D, 120C, and 120D of FIGS. 2C and 2D may determine the size, and shape of the of the resulting shear wave and/or tracking pulses. In some embodiments, the lenses 112C, 112D are removable such that differently focuses lenses may be interchangeably used depending on the desired operation of the transducers 110C, 110D, 120C, and 120D. In particular embodiments, the transducers 110A-110E and 120A-120E are formed of a shapeable piezocomposite material to provide a desired shape and beam formation.

Figure 2F:
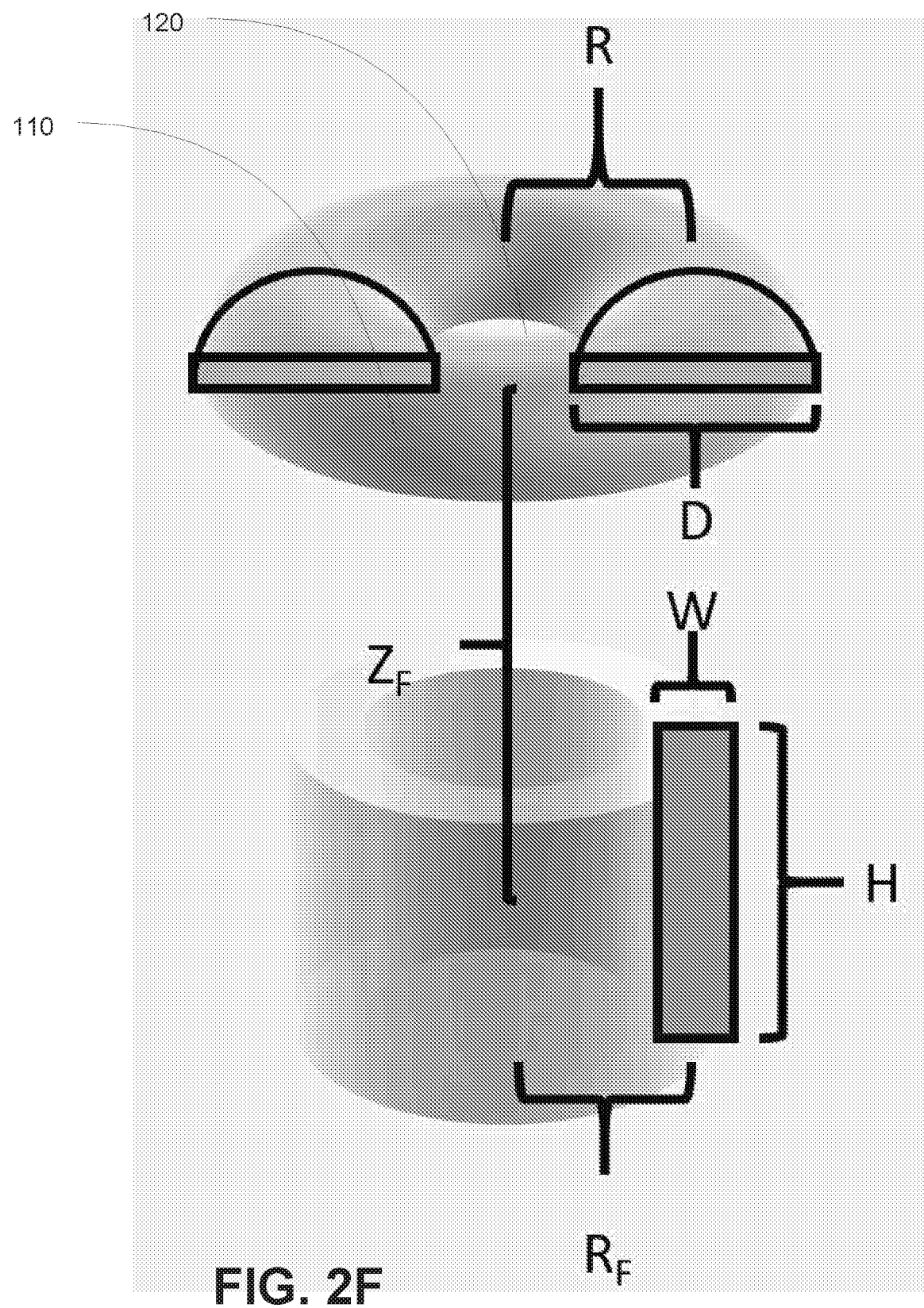

As shown in FIG. 2F the geometry of a hollow-cylindrical shear wave of finite extent can be focused by the transducer 110 (and tracked by the tracking transducer 120) and characterized by its height, H, its thickness W, its radius Rf, and its depth position Zf. Such a shear wave is generated from a transmitted pulse from a transducer, which can be characterized as having a frequency f0, a radius R, an initial width of D, and is shaped such that it is focused at the point (Rf, Zf). It will be understood that these geometric dimensions are approximations of a more complex geometry defined by the acoustic beam pattern of the transmitted wave.

A parameter called the F-Number F will be defined as the ratio of the distance between (R,0) and the focal point (Rf, Zf) to the aperture width D. The acoustic wavelength $\lambda$ will be defined as the speed of sound in the medium c divided by the center frequency f0. The F-Number F will have a typical range of 1-5, and the wavelength will have a range of about 0.02 mm to about 1 mm.

The height H, thickness W, radius Rf, and depth Zf of the hollow cylindrical shear wave are a function of the parameters of the excitation pulse, such that the thickness W is approximately the acoustic wavelength $\lambda$ times the F-Number F, the height will be approximately 9 times the wavelength $\lambda$ times the square of the F-Number F, and the focal point (Rf, Zf) specified by the shape of the excitation, pulse and set by time-delays on different individual element transmissions, the mechanical shape of the transducer, or, by time delays induced by an acoustic lens. The parameters of the excitation pulse may be chosen based on the geometry of the organ being, imaged. For example, skin may be imaged using a frequency of about 10-50 MHz and liver tissue may be imaged using a frequency of about 1-5 MHz Piezoelectric ultrasound transducers may be characterized by piezoelectric coefficients, and, in some embodiments, the shear wave generation transducer 110 may have different characteristics than the tracking transducer 120. The piezoelectric coefficient, $d_{33}$, the extensional strain constant, defines how much acoustic energy is generated for a given applied electric field, and dictates the transmit sensitivity of the transducer. The piezoelectric coefficient, $g_{33}$, the extensional voltage constant, defines bow much electric field (and thus voltage) is produced for a given acoustic field, and dictates the receive sensitivity of the transducer. The two-way sensitivity is dictated by both the transmit and receive properties, and is described by the intrinsic coupling coefficient $k_{33}$, or more generally, the effective coupling coefficient $k_{eff}$.

For the excitation element(s) of the transducer 110, a material may be optimized for efficient conversion of electrical signal into acoustic pressure ($d_{33}$), without regard for the receive sensitivity or coupling of the material ($g_{33}$ or $k_{33}$), since the element will only be used as a transmitter. For the receive elements, the coupling coefficients ($k_{33}$, $k_{eff}$) are of increased importance, as the receive elements must both transmit and receive, and should do so with minimal loss, Excitation elements such as the annular shear wave generation transducer 110 shown in FIG. 1 may therefore be constructed of a material having a higher extensional strain constant than the tracking transducer 120. Furthermore, the shear wave generation transducer 110 may vary in the geometric dimensions and acoustic backing and matching layer selections to further increase or optimize transmit power at the expense of bandwidth, because the acoustic radiation force pulses have very low bandwidth (<5% fractional BW), whereas tracking pulses (and thus the transducers such as the tracking transducer 120 that generates tracking pulses and receives echoes resulting from the tracking pulses) tend to be high bandwidth (>50% fractional BW) to maintain high, axial resolution. The pushing elements thus may also be constructed to have a higher quality factor Q than the tracking elements.

In certain embodiments, the shape of the wavefront used to excite the constructive shear wave may be shaped or adpodized by electronic or mechanical configuration. As illustrated in FIG. 3A, an annular shear wave generation transducer is shown, and an image of the resulting wavefront is shown in FIG. 3B. For anisotropic materials, whose viscoelastic properties vary with orientation, the measured constructive interference of an anisotropic shear wave may represent the properties of the tissue along the axis of anisotropy of the excitation. With anisotropic angular apodization, the cross-section of the constructive shear wave front can be shaped so that it has a directionality with respect to the orientation of the measured material. By varying the orientation of the excitation, the tissue properties can be interrogated along different axes.

In some embodiments, the shear wave generation transducer 110 may be electronically subdivided by angular sectors of the transducer, and the signals to each element may be delivered at different amplitudes, creating an axis of angular anisotropy. This may be a binary apodization (each sector is "on" or "off") or an arbitrary apodization (each sector uses an independently-specified signal).

As illustrated in FIGS. 4A and 5A (and corresponding respective images in FIGS. 4B and 5B), the shear wave generation transducer 110 may be apodized through the use of a lens or an absorbing mask 110M, which diverts or blocks sectors of the excitation pulse from reaching the focal region. The axis of angular anisotropy may be changed by mechanically rotating the mask or lens, or by selecting a different lens with a different apodization pattern. FIG. 4A illustrates two 90 degree sectors that are apodized through the mask 110M and FIG. 5A illustrates two 45 degree sectors that are apodized through the mark 110M.

Two apodization configurations and their impact on constructive shear waves in a transverse anisotropic material are shown in FIGS. 6A, 6B, 7A and 7B, in which the apodization of the excitation pulse is represented by a masked area 110M ("off") with other areas being "on." It should be understood, however, that the masked area 110M may be provided by electronically reducing the signal in the transducer 110, for example, by providing individually addressable transducers (e.g., wedge-shaped or linearly-shaped transducers) along the circumference of the annular transducer. The mask over the mask area 110M may be formed of an elastomeric material, such as an anechoic elastomer. The apodized excitation creates an anisotropic shear wave S in an anisotropic material 160, which is illustrated as anisotropic with higher elasticity along the fibers, which are oriented in alignment with the axis of angular anisotropy of the tissue 170. When the axis of anisotropy for the excitation 172 and the axis of anisotropy of the tissue 170 are perpendicular as shown in FIG. 6A, the material properties are interrogated across the fibers. When the axis of anisotropy for the excitation 172 and the axis of anisotropy of the tissue 170 are parallel as shown in FIG. 6A, the material properties are interrogated along the fibers. As, shown in the resulting shear wave displacement graphs of FIGS. 6B and 7B, the shear wave velocity in FIG. 6A is retarded relative to when the axes of anisotropy for the excitation and material aligned, as shown in FIG. 7A. Accordingly, the direction of anisotropy for an excitation may be determined by comparing shear wave velocity for apodization configurations, where the shear waves are faster when the excitation is aligned with the axes of anisotropy for the material.

Figure 8A:
Figure 8B:
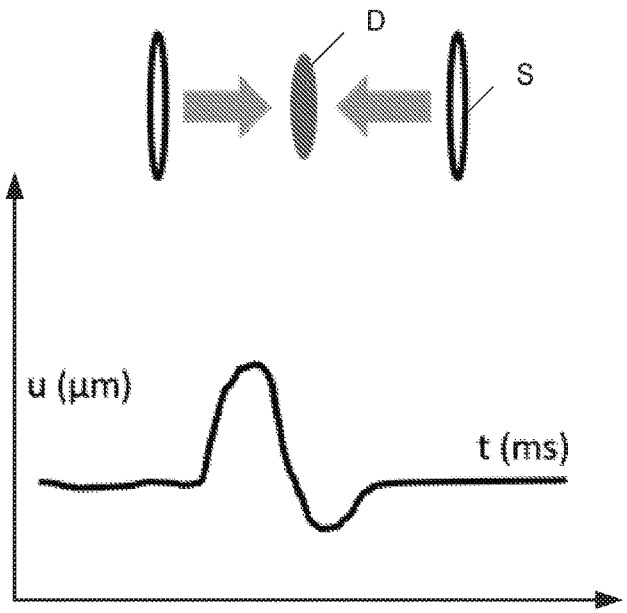

Although embodiments according to the invention are described with respect to cylindrical shear wave excitation, it should be understood that the shear wave excitation may be modified such that cylindrical excitations can have multiple cross sectional diameters. For example, FIG. 8A illustrates a cross-section of an annular array-type transducer 110 in which time-delayed ultrasound signals are delivered to the elements of the annular array transducer 110, For this "single-state" implementation, the array 110 may be replaced with a single element such as those described in FIGS. 2B-2D, whose acoustic signals are focused using either an acoustic lens or mechanical curvature. For the single-state configuration of FIG. 8A, there may be a series of 2 or more focused cylindrical pistons arranged in a ring. The resulting cross sectional shear wave S and the shear wave constructive displacement D is illustrated in the time-to-displacement graph shown in FIG. 8B.

Figure 9A:
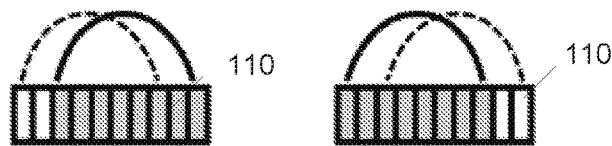
Figure 9B:
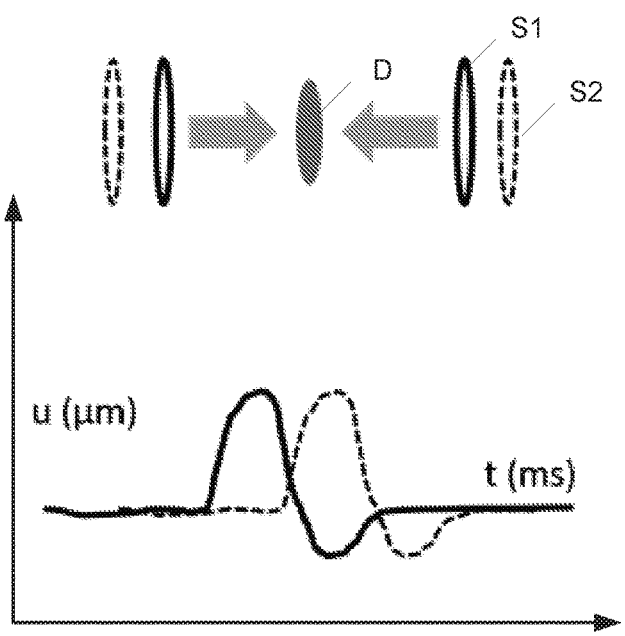

FIG. 9A illustrates a series of excitation pulses from the transducer 110 that produce two shear wave excitation cylindrical shapes S1, S2 at different diameters, which may be termed a "two-state" system. A switching mechanism allows for the selection of two, potentially overlapping, sets of elements to which to apply the time-delayed signals for shear wave generation. This allows for the generation of two different ring-type excitation foci of different radii (shear wave shapes S1, S2). Both shear wave shapes S1, S2 are tracked at the central location displacement D. The time-delay between the two recorded signals at the location of displacement D is indicative of the material's elastic properties when combined with (radial) distance between the focii as a shear wave speed, inverse shear wave speed, shear modulus (via c=sqrt(G/rho)) or shear compliance (1/G). Furthermore, shear wave attenuation may be estimated from the differences in shear wave amplitude measured at the location of the displacement D. The shear wave constructive displacement at the location of displacement D is illustrated in the time-to-displacement graph shown in FIG. 9B.

FIG. 10A illustrates a "slanted-ring focus" configuration in which the transducer array 110 emits excitation pulses at a timing to produce a cylindrical shape having a variable diameter as shown by the shear wave S. The shear wave constructive displacement at the location of displacement D is illustrated in the time-to-displacement graph shown in FIG. 10B. The shear wave radius varies with depth, allowing for tracking of multiple shear sources at different depths at the location of displacement D.

It should further be understood that shear waves can be generated with any number of radii. FIG. 11A illustrates an annular array transducer 110 that emits four shear wave excitations to generate shear waves S1-S4 that constructively interfere at a location of constructive displacement D. Each state or shear wave excitation causes a fixed set of delays to generate a ring focus at the specified radius. The shear wave constructive displacement at the location of displacement D is illustrated in the time-to-displacement graph shown in FIG. 11B.

Figure 12A:
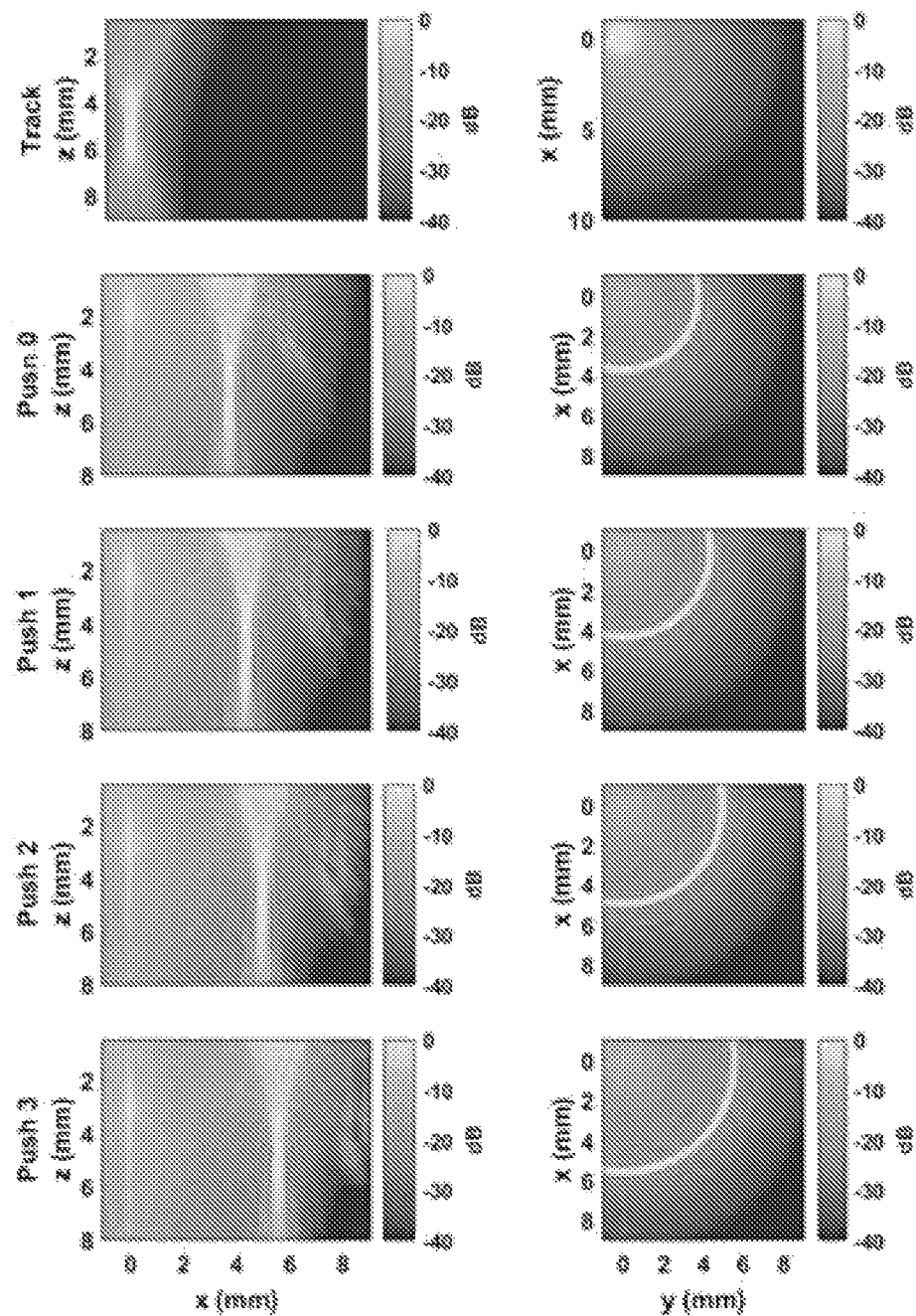
FIG. 12A are graphs illustrating a constructive shear wave simulation according to some embodiments.
Figure 12B:
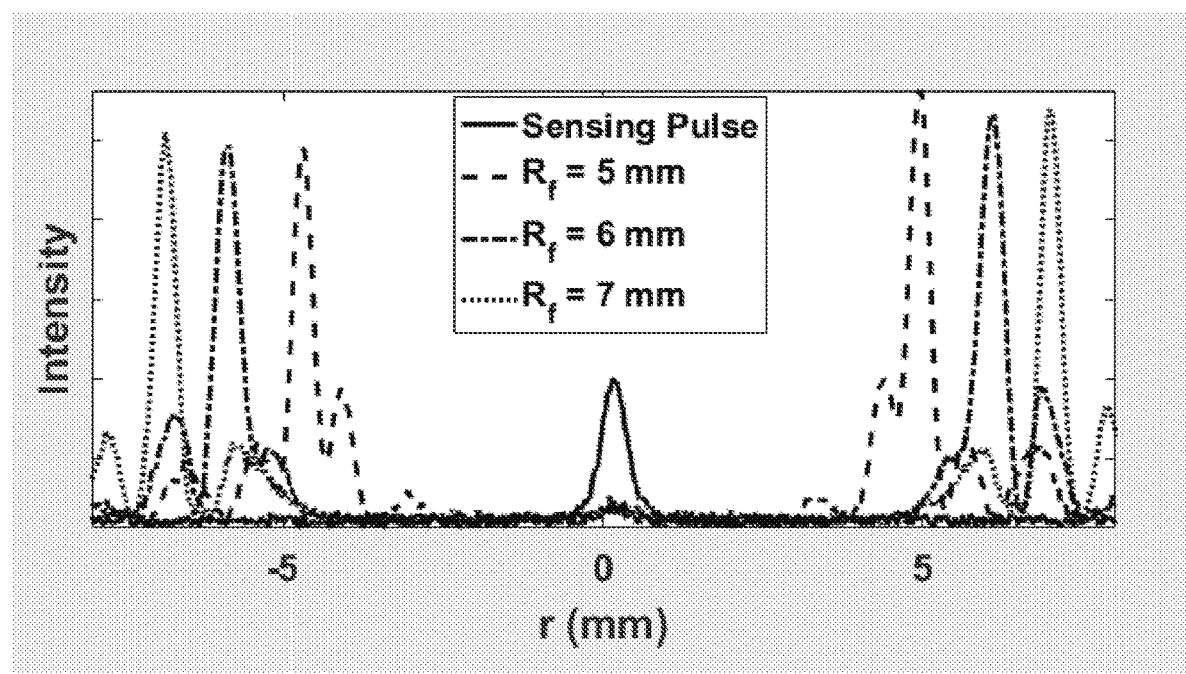
FIG. 12B is, a graph of plots of transmit pressure fields according to some embodiments.

Transmit pressure fields for the tracking piston and four states of push transmission were simulated using FIELD II Simulation Program. The results of the constructive shear wave simulation is illustrated in FIG. 12A. Using a prototype device, transmit pressure fields were measured in a water tank using a hydrophone. Plots of the transmit pressure fields are shown in FIG. 12B.

Figure 13A:
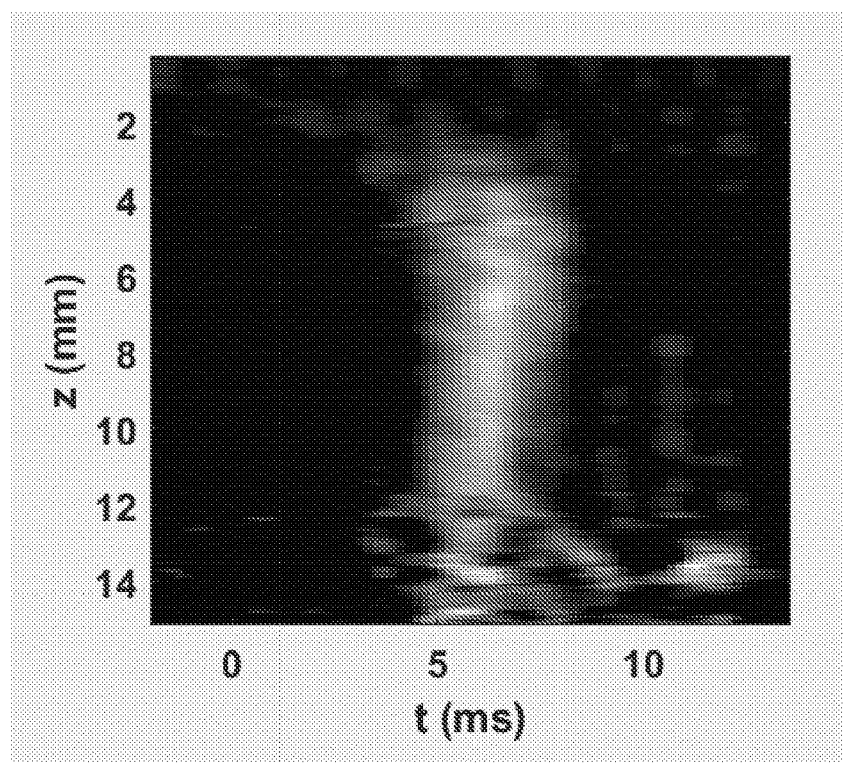
FIGS. 13A and 13B are n-mode images of displacement illustrating experimental validation data according to some embodiments.
Figure 13B:
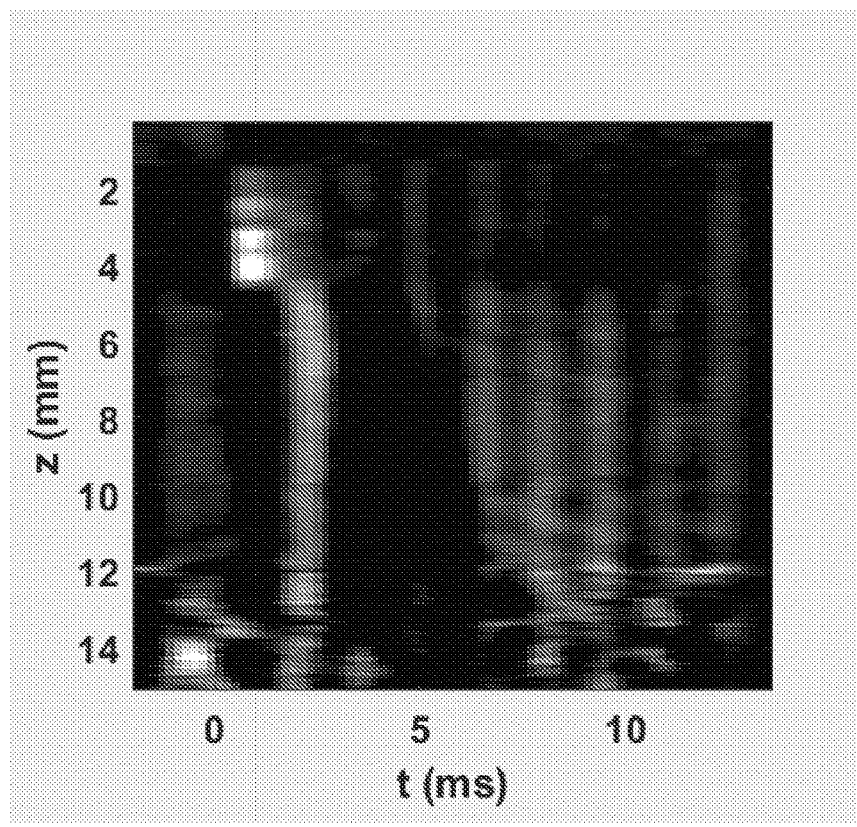

Experimental validation data are shown in FIGS. 13A-13B using typical parameters for imaging skin. The parameters of the excitation pulse are a frequency $f_0$ of 10 MHz, a pulse length of 40 us, a radial focus $R_f$ of 5 mm, a depth focus $Z_f$ of 10 mm, and an aperture width of 3 mm, resulting in a constructive shear wave of height>10 cm and thickness of 0.5 mm. The effective height of the shear wave is attenuated by the absorption of the material.

Figure 14:
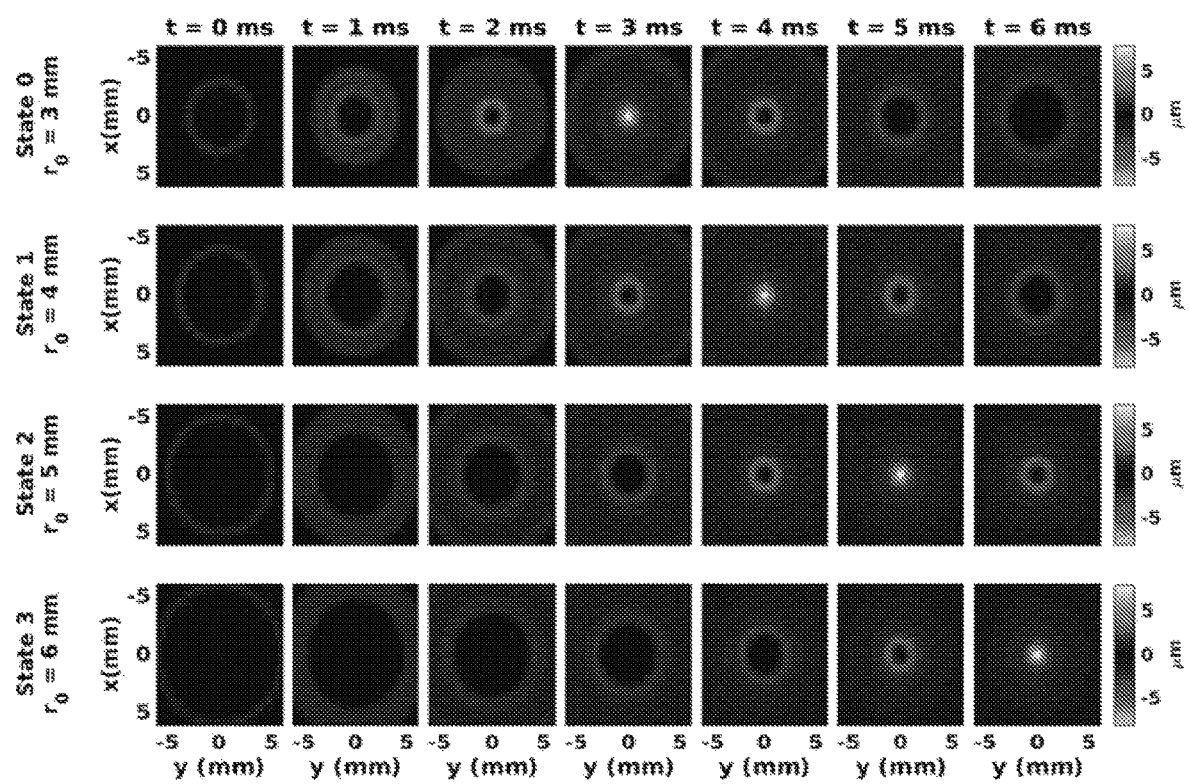
FIG. 14 illustrates the simulated propagation, of four ring shear waves according to some embodiments.

FIG. 14 illustrates the simulated propagation of four ring shear waves. The increase in amplitude upon constructive interference is illustrated.

An integrated annular transducer 110 and central tracking transducer 120 for an integrated handheld ultrasound transducer device 200 is shown in FIG. 15. A controller (computing unit such as a laptop, microcontroller, handheld computer, programmable integrated circuit etc.) may be used to control the transmit/receive of ultrasound data for the pulse-echo tracking transducer 120, for imaging the region of interest and to quantify the motion in the region of interest as determined by the transducer 120, and to control the higher power shear wave generation annular transducer 110.

FIG. 16 illustrates an annular transducer 110 that may be added to a tracking transducer 120 of an existing device 300. The tracking transducer 120 could include a cart-based ultrasound scanner, a handheld ultrasound scanner, or a single-element ultrasound piston connected to a pulser-receiver. The controller for the transducer 120 can operate as either a "master" or a "slave" to the added annular transducer 110. As a master, the controller would send a trigger-type signal to the existing ultrasound system that includes the transducer 120 to control when to acquire images, and would also control the shear wave generation annular transducer 110 to launch the constructive shear wave(s) at the appropriate time(s). As a slave, the controller would receive a trigger-type signal from the existing ultrasound system that includes the transducer 120, and generate the shear wave(s) on demand. This system would be physically affixed to the tracking transducer 120, either temporarily or permanently, and would leverage, the imaging capabilities of the existing system to track the induced motion.

The tracking signals may be detected and/or the shear waves may be generated repeated as described herein through a region of interest, for example, to generate an image. The tracking signals may be detected and/or the shear waves may be generated as described herein with an internally inserted ultrasound probe array or an externally applied ultrasound array. In some embodiments, the target region may be an in vivo human tissue sample; however, in vitro biomaterials, such as engineered tissues or hydrogels may be used.

The mechanical parameter(s) of the sample, such as shear elasticity modulus, Young's modulus, storage: modulus dynamic shear viscosity, shear wave velocity and mechanical impedance, can be correlated to measurement of healthy/diseased tissue states, such as by using actual clinical data and known healthy/diseased tissue states. The clinical data can be based on other factors such as demographic information, e.g., age, gender and race, to correlate the measurement of the mechanical parameter(s) with a measurement of healthy/diseased tissue states in a particular demographic group.

In some embodiments, the mechanical parameter(s) of the sample can be monitored as a function of time by performing the shear wave analyzing techniques described herein on a sample repeatedly over a period of time. A healthy/diseased tissue state determination can be based on a change in the mechanical parameter(s) as a function of time. For example, the mechanical parameter(s) can be monitored over a period of minutes, hours, days, weeks, months or even years to determine the progression of the disease and/or the efficacy of treatment.

In some embodiments, the mechanical parameter(s) may be used to form an ultrasound image, such as a B-mode image or an ARFI image.

The foregoing is illustrative of the present invention and is not to be construed as limiting thereof. Although a few example embodiments of this invention have been described, those skilled in the art will readily appreciate that many modifications are possible in the example embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein, That which is claimed is:

1. A transducer array comprising:
   a single annular shear wave generation transducer that defines an interior area, the single annular shear wave generation transducer being configured to generate a shear wave excitation to a region of interest,
   wherein the region of interest comprises a cylindrical excitation region of interest comprising a hollow cylinder shear wave excitation region, and an interior region of interest comprising a solid cylinder interior region defined by an inner portion of the hollow cylinder shear wave excitation region,
   the single annular shear wave generation transducer having at least one of 1) an annular concave shape for focusing the shear wave excitation and 2) a focusing lens for focusing the shear wave excitation, wherein the single annular shear wave generation transducer is configured such that the shear wave excitation comprises a single excitation focused so as to excite at least a partial angular section of the cylindrical excitation region of interest and shear waves propagating from the cylindrical excitation region of interest constructively interfere in the interior region of interest; and
   at least one tracking transducer positioned in the interior area of the single annular shear wave generation transducer, the at least one tracking transducer being configured to detect a shear wave in the interior region of interest.

2. The transducer array of claim 1, wherein the single annular shear wave generation transducer has a higher extensional strain constant than the at least one tracking transducer.

3. The transducer array of claim 1, wherein the single annular shear wave generation transducer comprises a concave annular transducer shape that focuses the shear wave excitation to excite the at least a partial angular section of the cylindrical excitation region of interest.

4. The transducer array of claim 1, wherein the single annular shear wave generation transducer comprises the focusing lens, and the focusing lens is on a face of the single annular shear wave generation transducer.

5. The transducer array of claim 1, wherein the at least one tracking transducer comprises an array of concentric tracking transducers.

6. The transducer array of claim 1, wherein the at least one tracking transducer comprises a concave tracking element.

7. The transducer array of claim 1, further comprising a focusing lens on a face of the at least one tracking transducer configured to focus a tracking pulse to the interior region of the region of interest where shear waves generated by the shear wave excitation constructively interfere.

8. The transducer array claim 1, further comprising an apodized portion of the annular shear wave generation transducer, wherein the apodized portion has a reduced or eliminated shear wave excitation therefrom.

9. A transducer array assembly comprising:
   a transducer array comprising:
      at least one annular shear wave generation transducer that defines an interior area; and
      at least one tracking transducer positioned in the interior area of the at least one annular shear wave generation transducer; and
   a controller configured to control the at least one annular shear wave generation transducer to generate a shear wave excitation to a region of interest, wherein the region of interest comprises a cylindrical excitation region of interest comprising a hollow cylinder shear wave excitation region, and an interior region of interest comprising a solid cylinder interior region defined by an inner portion of the hollow cylinder shear wave excitation region, such that the shear wave excitation comprises a single excitation focused so as to excite at least a partial angular section of the cylindrical excitation region of interest and shear waves propagating from the cylindrical excitation region of the region of interest constructively interfere in the interior region of interest, and to control the at least one tracking transducer to detect a shear wave in the interior region of interest.

10. The transducer array assembly of claim 9, wherein the at least one annular shear wave generation transducer has a higher extensional strain constant than the at least one tracking transducer.

11. The transducer array assembly of claim 9, wherein the at least one annular shear wave generation transducer comprises an array of concentric annular transducers.

12. The transducer array assembly of claim 9, wherein the at least one annular shear wave generation transducer comprises a concave annular transducer.

13. The transducer array assembly of claim 9, further comprising a focusing lens on a face of the annular shear wave generation transducer.

14. The transducer array assembly of claim 9, wherein the at least one tracking transducer comprises an array of concentric tracking transducers.

15. The transducer array assembly of claim 9, wherein the at least one tracking transducer comprises a concave tracking element.

16. The transducer array assembly of claim 9, further comprising a focusing lens on a face of the at least one tracking transducer configured to focus a tracking pulse to the interior region of interest where shear waves generated by the shear wave excitation constructively interfere.

17. The transducer array assembly of claim 9, wherein the controller is configured to control the at least one tracking transducer to detect a shear wave in the interior region of interest by emitting at least one tracking pulse.

18. The transducer array assembly of claim 9, further comprising an apodized portion of the annular shear wave generation transducer, wherein the apodized portion has a reduced or eliminated shear wave excitation therefrom.

19. The transducer array assembly of claim 9, further comprising a mask configured to reduce or eliminate the shear wave excitation from a portion of the annular shear wave generation transducer.

20. The transducer array assembly of claim 9, wherein the controller is further configured to characterize the region of interest based on the shear wave detected by the at least one tracking transducer.

21. A method of generating a constructive shear wave for characterizing a region of interest, the method comprising
providing a transducer array comprising:
at least one annular shear wave generation transducer that defines an interior area; and
at least one tracking transducer positioned in the interior area of the at least one annular shear wave generation transducer, wherein the region of interest comprises a cylindrical excitation region of interest comprising a hollow cylinder shear wave excitation region, and an interior region of interest comprising a solid cylinder interior region defined by an inner portion of the hollow cylinder shear wave excitation region; and
controlling the at least one annular shear wave generation transducer to generate a shear wave excitation to a region of interest such that the shear wave excitation comprises a single excitation focused so as to excite at least a partial angular section of the cylindrical excitation region of interest and shear waves propagating from the cylindrical excitation region of interest constructively interfere in the interior region of interest; and
controlling the at least one tracking transducer to detect a shear wave in the interior region of interest.

* * * * *